United States Patent [19]

Schwan

[11] 4,052,399
[45] Oct. 4, 1977

[54] 1-[2-(HEXAHYDRO-1H-AZEPINO)ETHYL]-2(1H)PYRIMIDONE DIHYDROCHLORIDE

[75] Inventor: Thomas J. Schwan, Norwich, N.Y.

[73] Assignee: Morton-Norwich Products, Inc., Norwich, N.Y.

[21] Appl. No.: 722,564

[22] Filed: Sept. 13, 1976

[51] Int. Cl.$^2$ ............................................. C07D 403/06
[52] U.S. Cl. ................................................ 260/256.4 C
[58] Field of Search ................................... 260/256.4 C

[56] References Cited

U.S. PATENT DOCUMENTS

| | | | |
|---|---|---|---|
| 3,681,349 | 8/1972 | Schwan et al. | 260/256.4 C |
| 3,941,789 | 3/1976 | Renth et al. | 260/256.4 C |

Primary Examiner—Donald G. Daus
Assistant Examiner—James H. Turnipseed
Attorney, Agent, or Firm—Anthony J. Franze

[57] ABSTRACT

1-[2-(Hexahydro-1H-azepino)ethyl]-2(1H)pyrimidone dihydrochloride possesses pharmacological activity as a hypotensive agent.

1 Claim, No Drawings

1-[2-(HEXAHYDRO-1H-AZEPINO)ETHYL]-2(1H)PYRIMIDONE DIHYDROCHLORIDE

This invention relates to a compound of the formula:

When administered intravenously to animals this compound exhibits hypotensive activity. Administration of from 50 to 100 mg/kg of this compound intravenously to anesthetized dogs resulted in hypotensive activity lasting for as long as 2½ hours.

In order that this invention be readily available to and understood by those skilled in the art the following illustrative example is included:

1-[2-(Hexahydro-1H-azepino)ethyl]-2(1H)pyrimidone dihydrochloride

To a solution of 2-hydroxypyrimidine hydrochloride (39.9 g, 0.3 mole) in 700 mls of methanol was added potassium carbonate (124 g, 0.9 mole), sodium iodide (5 g), 2-(hexahydro-1H-azepino)ethyl]chloride hydrochloride (59 g, 0.3 mole) and 200 mls of methanol. The suspension was refluxed for 24 hrs and concentrated to dryness in vacuo. The residue was diluted with water (300 mls) and extracted with chloroform (3 × 300 mls). The chloroform extracts were combined, washed with water (2 × 100 mls) and then dried over magnesium sulfate. The free base (56 g, 85%) was recovered after concentration of the chloroform in vacuo.

The product 37 g (82%) was prepared by dissolving the free base (33 g) in methanol and treating the solution with methanolic hydrogen chloride.

An analytical sample, m.p. dec. 195°, was obtained by recrystallization from ethanol (25 ml/gm).

Anal. Calcd. for $C_{12}H_{19}N_3O.2HC$: C, 48,99; H, 7.20; N, 14.28. Found: C, 48.93; H, 7.08; N, 14.26.

What is claimed is:

1. The compound of the formula:

* * * * *